(12) United States Patent
Chodankar et al.

(10) Patent No.: US 6,812,355 B2
(45) Date of Patent: Nov. 2, 2004

(54) PROCESS FOR THE MANUFACTURE OF CITALOPRAM HYDROBROMIDE FROM 5-BROMOPHTHALIDE

(75) Inventors: Nandkumar Chodankar, Mumbai (IN); Ajit Bhobhe, Mumbai (IN); Ganesh Mukund Oak, Thane (IN); Philip Eappen, Dombivli (IN)

(73) Assignee: Sekhsaria Chemicals Limited, Mumbai (IN)

( * ) Notice: Subject to any disclaimer, the term of this patent is extended or adjusted under 35 U.S.C. 154(b) by 71 days.

(21) Appl. No.: 10/277,451

(22) Filed: Oct. 22, 2002

(65) Prior Publication Data
US 2004/0077870 A1 Apr. 22, 2004

(51) Int. Cl.$^7$ ............................................. C07D 307/87
(52) U.S. Cl. ........................................................ 549/467
(58) Field of Search ........................................ 549/467

(56) References Cited

U.S. PATENT DOCUMENTS

| | | | |
|---|---|---|---|
| 3,467,675 A | | 9/1969 | Petersen et al. |
| 4,136,193 A | * | 1/1979 | Bogeso et al. ............. 514/469 |
| 4,587,256 A | | 5/1986 | Hasler et al. |
| 4,650,884 A | | 3/1987 | Bogeso |
| 4,933,361 A | | 6/1990 | Urbach et al. |
| 4,999,370 A | | 3/1991 | Rilger et al. |
| 5,061,722 A | | 10/1991 | Teetz et al. |
| 6,229,026 B1 | | 5/2001 | Petersen |
| 6,310,222 B1 | | 10/2001 | Ikemoto et al. |
| 6,365,747 B1 | | 4/2002 | Dall'Asta et al. |
| 2001/0031784 A1 | | 10/2001 | Petersen et al. |
| 2001/0031874 A1 | | 10/2001 | Connor et al. |
| 2001/0049450 A1 | | 12/2001 | Ikemoto et al. |
| 2002/0040153 A1 | | 4/2002 | Petersen |
| 2002/0115872 A1 | | 8/2002 | Hilden et al. |

FOREIGN PATENT DOCUMENTS

| | | |
|---|---|---|
| CA | 2291067 | 5/1998 |
| DE | 2657013 C2 | 11/1985 |
| DE | 698 01 764 T2 | 9/2001 |
| EP | 0 171 943 A1 | 2/1986 |
| EP | 0 347 066 B1 | 6/1989 |
| EP | 1 015 416 B1 | 9/2001 |
| JP | 06329636 | 11/1994 |
| WO | WO 98/19511 A2 | 5/1998 |
| WO | WO 98/19512 A2 | 5/1998 |
| WO | WO 98/19513 A3 | 5/1998 |
| WO | WO 98/19513 A2 | 5/1998 |
| WO | WO 99/30548 A3 | 6/1999 |
| WO | WO 99/30548 A2 | 6/1999 |
| WO | WO 00/23431 A1 | 4/2000 |
| WO | WO 01/80619 A2 | 11/2001 |
| WO | WO 01/80619 A3 | 11/2002 |

OTHER PUBLICATIONS

International Search Report of EP 02 25 5750 dated Oct. 24, 2002.

* cited by examiner

*Primary Examiner*—Patricia L. Morris
(74) *Attorney, Agent, or Firm*—Caesar, Rivise, Bernstein, Cohen & Pokotilow, Ltd.

(57) ABSTRACT

A process for the preparation of 1-(4'-fluorophenyl)-1-(3-dimethylamino-propyl)-5-phthalanecarbonitrile of formula (I), or a pharmaceutically acceptable salt thereof,

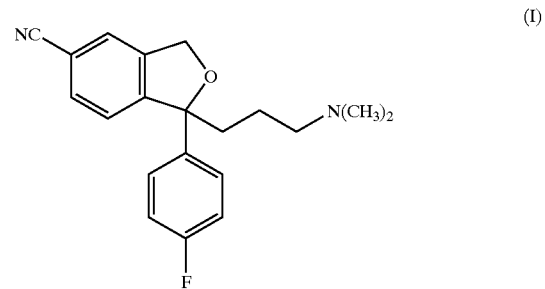

comprising performing two successive Grignard reactions on 5-bromophthalide, wherein the 5-bromophthalide is reacted with the first Grignard reagent in the presence of a Lewis acid, so reducing by-product formation and improving yields.

4 Claims, No Drawings

PROCESS FOR THE MANUFACTURE OF CITALOPRAM HYDROBROMIDE FROM 5-BROMOPHTHALIDE

The present invention relates to a process for preparing 1-(4'-fluorophenyl)-1-(3-dimethylaminopropyl)-5-phthalanecarbonitrile ("citalopram") or a pharmaceutically acceptable salt thereof. In particular, the present invention relates to an improved process for preparing citalopram hydrobromide from 5-bromophthalide.

Citalopram is a bicyclic phthalane derivative of the formula (I), which has been found to have useful therapeutic activity, particularly as an antidepressant.

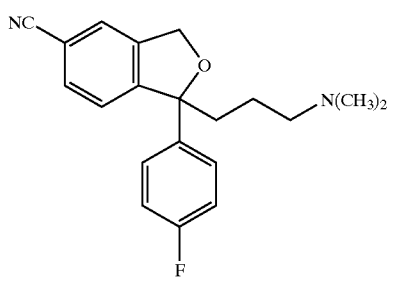

(I)

The preparation of citalopram and its hydrobromide salt from 5-bromophthalide and the properties of such compounds was first reported in U.S. Pat. No. 4,136,193, which corresponds to German Offenlegungsschrift No. 2,657,013. U.S. Pat. No. 4,136,193 discloses a synthesis of citalopram starting from 5-bromophthalide, which involves the use of two successive Grignard reactions. In a first reaction, a Grignard reagent prepared from p-fluorobromobenzene and magnesium turnings in ether was reacted with 5-bromophthalide to give 2-hydroxymethyl-4-bromo-4'-fluorobenzophenone. The latter was isolated as a crude oil before, in a second reaction, being added to N,N-dimethylaminopropylymagnesium chloride to give (4-bromo-2-(hydroxymethyl)phenyl)-(4'-fluorophenyl)-(3-dimethylaminopropyl)-methanol. The latter was dehydrated with 60 aqueous phosphoric acid to yield 1-(4'-fluorophenyl)-1-(3-dimethylaminopropyl)-5-bromophthalane, which was then refluxed with cupric cyanide in dimethylformamide to give citalopram.

A number of other processes have been reported for the manufacture of citalopram hydrobromide. Subsequent patents indicate that 5-cyanophthalide should be used as a raw starting material giving the reason that the method disclosed in U.S. Pat. No. 4,136,193 is not a good one because of the inherent problems involved, the main difficulties faced being due to the Grignard Reactions and the replacement of the bromo group by the cyano group. It is an object of the present invention to try to resolve such difficulties by the use of specific reagents and simple techniques.

Moreover, in U.S. Pat. No. 4,136,193, process details were not discussed in any detail. It is an object of the present invention to describe not only the manufacturing technology in detail, but also the purification carried out at each stage to achieve citalopram of pharmaceutical grade purity, as well as additional purification methods using water as a solvent. The present invention therefore relates to an improved process for the manufacture of citalopram hydrobromide and other salts of citalopram, such as its hydrochloride, acetate and oxalate, from 5-bromo- and other 5-halophthalides.

Accordingly, in a first aspect of the invention, there is provided a process for the preparation of a compound of the formula (XX)

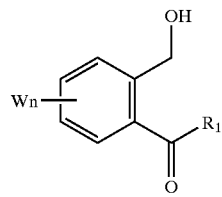

(XX)

wherein $R_1$ is a substituted or unsubstituted alkyl, alkenyl, alkynyl, cycloalkyl, cycloalkenyl, cycloalkynyl, aryl or aralkyl group, optionally including at least one heteroatom in its carbon skeleton, W is a halogen, cyano or hydroxyl group, or an unsubstituted alkyl, alkenyl, alkynyl, cycloalkyl, cycloalkenyl, cycloalkynyl, aryl or aralkyl group, optionally containing at least one heteroatom in its carbon skeleton, and n is an integer from 0 to 4, with the proviso that, when n>1, each W group may be the same or different, which process comprises the step of reacting a phthalide of the formula (XXI)

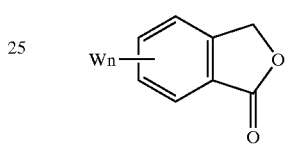

(XXI)

with a Grignard reagent of the formula (XXII)

$R_1$—MgY        (XXII)

wherein Y represents halogen, characterised in that the phthalide of formula (XXI) is reacted with 2 Lewis acid to form an adduct, prior to reaction with the Grignard reagent of formula (XXII).

Reactions involving the addition of Grignard reagents to carbonyl compounds can be unreliable, often giving poor yields or unwanted by-products. This is particularly true in the case of branched ketones which may be reduced to the corresponding carbinols. Such reactions frequently require the use of a high molar excess of the Grignard reagent based on the amount of ketone (e.g., at least two equivalents of the Grignard reagent), which can render the process uneconomical. Moreover, in the case of reactions involving the addition of Grignard reagents to lactones, the use of a high molar excess of the Grignard reagent could also result in the addition of a second molecule of the Grignard reagent to the same carbonyl group, after opening of the lactone ring. It is known that the addition of Grignard reagents to certain simple ketones can be catalysed by Lewis acids. However, it is believed that the use of Lewis acids to catalyse the addition of Grignard reagents to phthalides has not previously been disclosed.

Advantageously, the use of a Lewis acid to catalyse addition of a Grignard reagent to a phthalide can help suppress formation of the corresponding carbinol and can improve yields of the desired ketone. In addition, the amount of the Grignard reagent used may be reduced, thereby limiting the possibility of the newly formed ketone group undergoing further reactions, as well as rendering the process more cost effective on an industrial scale. It is believed that the Lewis acid may form a co-ordination complex with the oxygen atom of the carbonyl group in the lactone ring of the phthalide of formula (XXI) or with the oxygen atom in the heterocyclic ring. However, the exact mechanism involved is not fully understood and is most probably more complex (it is for this reason that it is difficult to make any reliable predictions about the efficacy of Grignard reactions and likely catalysis).

In the invention in its first aspect, $R_1$ may be any substituted or unsubstituted alkyl, alkenyl, alkynyl, cycloalkyl, Cycloalkenyl, cycloalkynyl, aryl or aralkyl group, optionally including at least one heteroatom in its carbon skeleton. In a preferred embodiment, $R_1$ is a substituted or unsubstituted aryl or aralkyl group, such as a phenyl or benzyl group, or an alkyl group having from 1 to 8, preferably from 1 to 4, carbon atoms, such as a methyl or t-butyl group. W may be a halogen, cyano or hydroxyl group, or any unsubstituted alkyl, alkenyl, alkynyl, cycloalkyl, cycloalkenyl, cycloalkynyl, aryl or aralkyl group, optionally containing at least one heteroatom in its carbon skeleton. In a preferred embodiment, W is a halogen group, preferably a bromine, chlorine or fluorine group, a bromine group being especially preferred. n may be any integer from 0 to 4, with the proviso that, when n is greater than 1, such that more than one W substituent is present, each W may be the same or different. The Lewis acid is generally present in equimolar amount or in molar excess based on the amount of the phthalide of formula (XXI), although this is not essential. In a preferred embodiment, the Lewis acid is generated in situ, prior to reaction with the phthalide of formula (XXI). The phthalide of formula (XXI) may then be added to the freshly, prepared Lewis acid, which is both convenient and ensures that the Lewis acid is at its most active. In a preferred embodiment, the resultant adduct of the phthalide of formula (XXI) and the Lewis acid is then reacted in situ with the Grignard reagent of formula (XXII). Preferably, the adduct of the phthalide of formula (XXI) and the Lewis acid is reacted with the Grignard reagent of formula (XXII) at a temperature below 20° C., preferably at a temperature below 10° C., and preferably at a temperature of between about −10 to 5° C. In a most preferred embodiment, the Lewis acid is a magnesium halide, preferably magnesium bromide. In the latter case, the magnesium bromide may be generated in situ by reaction of magnesium turnings with 1,2-dibromoethane. In a preferred embodiment, the process according to the invention in its first aspect is for the preparation of a 2-hydroxymethyl-4-halo-4'-fluorobenzophenone of the formula (IV)

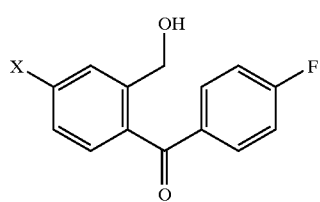

(IV)

and comprises reacting a magnesium halide with a 5-halophthalide of the formula (II)

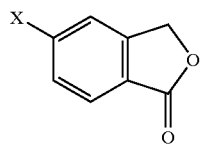

(II)

wherein X represents halogen, to form a 5-halophthalide/magnesium halide adduct, and reacting the adduct so obtained with a Grignard reagent of the formula (III)

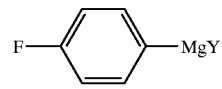

(III)

wherein Y represents halogen, to form the 2-hydroxymethyl-4-halo-4'-fluoro-benzophenone of formula (IV).

In a second aspect of the invention, there is provided a process for the preparation of 1-(4'-fluorophenyl)-1-(3-dimethylamino-propyl)-5-phthalanecarbonitrile of the formula (I), or a pharmaceutically acceptable salt thereof,

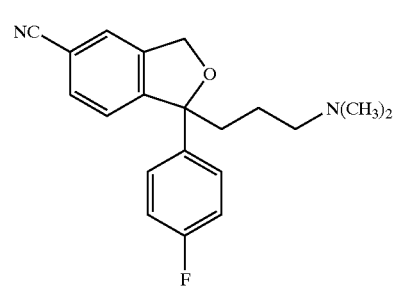

(I)

which comprises the step of preparing a 2-hydroxymethyl-4-halo-4'-fluoro-benzophenone of the formula (IV) by a process according to the invention in its first aspect. In a preferred embodiment, the process further comprises the step of reacting the 2-hydroxymethyl-4-halo-4'-fluorobenzophenone of formula (IV)

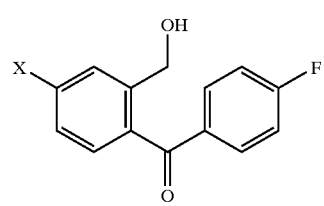

(IV)

with a Grignard reagent of the formula (V)

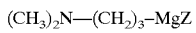

(CH$_3$)$_2$N—(CH$_2$)$_3$—MgZ    (V)

to form a 1-(4-halo-2-hydroxymethylphenyl)-1-(4'-fluorophenyl)-1-(3-dimethyl-aminopropyl)methanol of the formula (VI)

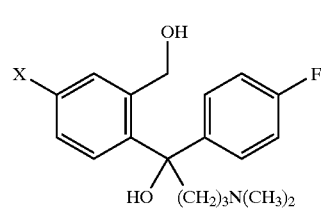

(VI)

In the latter embodiment, the 2-hydroxymethyl-4-halo-4'-fluorobenzophenone of formula (IV) is preferably not isolated, prior to reaction with the Grignard reagent of formula (V). In this case, the Grignard reagent of formula (V) may be added to a solution of the 2-hydroxymethyl-4-halo-4'-fluorobenzophenone of formula (IV), thereby obviating the need to isolate or purify the latter prior to reaction with the Grignard reagent of formula (V) with associated yield reduction. Such a possibility considerably: facilitates the final synthetic route and was previously not viable on account of the low yields of the 2-hydroxymethyl-4-halo-4'-fluorobenzophenone of formula (IV) and high incidence of by-products formed during conventional procedures for addition of a Grignard reagent of the formula (III) to a 5-halophthalide of the formula (II). In embodiments of the invention in its first or second aspects, X, Y and Z are each, independently, chlorine, bromine or iodine. X and Y are preferably each bromine, and Z is preferably chlorine. Preferably, the two successive Grignard reactions are carried out in situ at a temperature of less than about 30° C., preferably less than about 20° C., and preferably at a temperature of from 5 to −10° C. In this case, the Grignard reagents may be formed at higher temperatures, but may then be cooled to the desired temperature before the reaction takes place. In another embodiment, the inventive process further comprises the step of dehydrating the 1-(4-halo-2-hydroxymethylphenyl)-1-(4'-fluoro-phenyl)-1-(3-dimethylaminopropyl)methanol of formula (VI), to form a 1-(4'fluorophenyl)-1-(3-dimethylaminopropyl)-5-halophthalane of the formula (VIII)

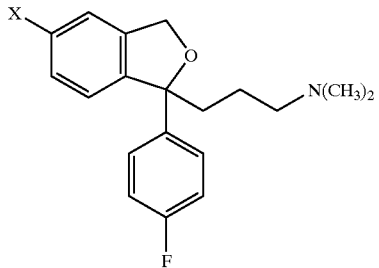

(VIII)

Any conventional dehydrating agents may be used in this reaction, although the use of very strong or concentrated dehydrating agents is generally undesirable as this may result in degradation and formation of unwanted by-products. 50% aqueous phosphoric acid is especially preferred in this regard. In a preferred embodiment, tile process further comprises the step of reacting the 1-(4'fluorophenyl)-1-(3-dimethylaminopropyl)-5-halophthalane of formula (VIII) with a cyanating agent, such as copper cyanide, to form 1-(4'-fluorophenyl)-1-(3-dimethylaminopropyl)-5-phthalanecarbonitrile of formula (I). The cyanation reaction is preferably carried out in the presence of an iodide salt, such as potassium iodide. In a preferred embodiment, the cyanation reaction is carried out in the presence of a monosaccharide, a disaccharide or a polysaccharide, preferably dextrose. The cyanation is also preferably carried out at moderate to high temperature, especially at a temperature of from 120 to 200° C., preferably from 130 to 180° C., most preferably from 140 to 160° C. Any suitable solvent may be used for the cyanation reaction, although dimethylformamide is especially preferred. In a preferred embodiment, the crude 1-(4'-fluorophenyl)-1-(3-dimethylaminopropyl)-5-phthalanecarbonitrile of formula (I) may be converted into an acid addition salt and the latter may be extracted into an aqueous phase of a bi-phasic solvent system. Preferably, the 1-(4'-fluorophenyl)-1-(3-dimethylamino-propyl)-5-phthalane-carbonitrile of formula (I) is converted into its hydrobromide, acetate or oxalate salt. If desired, the acid addition salt may be further purified by recrystallization from a suitable solvent, such as water. This has been found to be particularly effective in the case of citalopram hydrobromide, which can be obtained in a high degree of purity by recrystallization one or more times from water as a final purification step.

Accordingly, in a third aspect of the invention, there is provided purified citalopram hydrobromide obtainable by recrystallization from water of citalopram hydrobromide prepared by the process according to the invention in its second aspect. Preferably, citalopram hydrobromide so obtained has a purity of at least 99% by weight, preferably at least 99.50% by weight, more preferably at least 99.75% by weight, most preferably at least 99.99% by weight.

In order that the invention may be more fully understood, it will now be described by way of illustration only, with reference to the following specific examples.

(4-bromo-2-(hydroxymethyl)phenyl)-(4'-flourophenyl)-(3-dimethylaminopropyl) methanol A Grignard solution was prepared from p-fluorobromobenzene (197.6 g) and magnesium turnings (28.15 g) in tetrahydrofuran (1250 ml), in the presence of 1,2-dibromoethane and iodine. The Grignard solution was added to a suspension in tetrahydrofuran (1050 ml) of 5-bromophthalide (150 g) and magnesium bromide, prepared in situ from magnesium and 1,2-dibromoethane over a period of two hours at a temperature below 20° C. After addition was complete, the mixture was stirred, and a Grignard solution of N,N-dimethylaminopropylmagnesium chloride was added to the solution over a period of time at a temperature below 20° C. for more than one hour. The result was mixture was poured into saturated ammonium chloride solution (4500 ml) over a period of time at a temperature below 30° C.

The tetrahydrofuran layer was separated, washed free of excess alkali and distilled under reduced pressure. Toluene was added to the residue and extracted with 20% acetic acid to acidic reaction. The acetate salt was purified, made alkaline with 10% aqueous sodium hydroxide, extracted in toluene and the solvent distilled under reduced pressure to give reasonably pure 4-bromo-2-(hydroxymethyl)phenyl-(4-fluorophenyl)-3-(dimethylaminopropyl)methanol.

1-(4'-fluorophenyl)-1-(3-dimethylaminopropyl)5-bromophthalane

The (4-bromo-2-(hydroxymethyl)phenyl)-(4'fluorophenyl)-(3-dimethylamino-propyl)methanol residue (160 g) was heated with 50% aqueous phosphoric acid (1.99 kg) with vigorous stirring. The reaction mass was purified by extraction and neutralized with aqueous ammonia at a temperature below 30° C. The reaction mass was extracted with toluene and the solvent distilled under reduced pressure to give 1-(4'fluorophenyl)-1-(3-dimethylaminopropyl)-5-bromophthalane (130 g).

1-(4'-fluorophenyl)-1-(3-dimethylaminopropyl)-5-phthalanecarbonitrile hydrobromide 1-(4'-fluorophenyl)-1-(3-dimethylaminopropyl)-5-bromophthalane (130 g), cuprous cyanide (129.6 g in 2 to 4 lots), potassium iodide and dextrose in dimethyl-formamide were heated together at 140–160° C., to give 1-(4'-fluorophenyl)-1-3-dimethylaminopropyl)-5-phthalane-carbonitrile (citalopram). The crude citalopram was purified and converted to its hydrobromide by one of the following methods.

Purification Process I

After the reaction was complete, tie dimethylformamide was partially recovered (about 65%), toluene (325 ml) was added and aqueous ammonia (325 g) charged to the reaction vessel at a temperature above 50° C. The reaction mixture was stirred and cooled to 20° C. The reaction mass was filtered and the residue was leached with toluene and aqueous ammonia once again. The toluene layers were combined and the aqueous layer was separated. The toluene layer was washed repeatedly with aqueous ammonia and then with demineralized water. Methanol (50 ml) was added to the toluene layer, and the latter was washed with water (800 ml). The organic layer was washed repeatedly with 0.05% solution of hydrobromic acid. The toluene layer was extracted twice with 20% acetic acid to obtain a pH of 4.5 to 4.8. The combined aqueous layers were extracted repeatedly with toluene at a pH of 4.5 to 4.8. The aqueous layer was made alkaline with 10% aqueous sodium hydroxide and the product was extracted with toluene (260 ml). The aqueous layer was separated and extracted twice with toluene (about 50 ml). To the residue so obtained, toluene was added (1.5 times by volume) and mixture treated with Hyflo®. The solution was cooled to 20° C. and n-hexane (5.5 times by volume) was added slowly. The solution was then stirred for about 30 minutes and filtered. The toluene/n-hexane layer was treated with silica and charcoal at about 60° C., and the solution filtered. The silica bed was washed with n-hexane, and the toluene/n-hexane layer was concentrated under vacuum. To the oily residue were added ethyl acetate and demineralized water. In another flask, a solution of oxalic acid in ethyl acetate was prepared by heating to a temperature of 65 to 70° C. The solution was cooled to 55 to 60° C. and added to the base in ethyl acetate at a temperature of about 50 to 55° C. The resultant solution was stirred at 65° C. for about 30 minutes, before being cooled slowly to 0 to 5° C. and filtered. The oxalate salt was washed with chilled ethyl acetate and n-hexane and dried. The dried oxalate salt so obtained was dissolved in water. The salt was converted to the free base using 5% aqueous sodium hydroxide and extracted in toluene. The aqueous layer was repeatedly extracted with toluene. The combined toluene layers were washed with dimineralized water, and the toluene was distilled off under vacuum. Any traces of toluene were removed, isopropyl alcohol was added and the resultant solution was treated with activated carbon at 40 to 45° C. The solution was then filtered and aqueous hydrobromic acid was added at 30 to 35° C. to obtain a pH of 5.4 to 5.5. The resultant solution was cooled to 0 to 5° C., filtered and dried to give pure citalopram hydrobromide.

Purification Process II

After the reaction was complete, the dimethylformamide was partially recovered (about 65%) and toluene (325 ml) was added and aqueous ammonia (325 g) charged to the reaction vessel at a temperature above 50° C. The reaction mixture was stirred and cooled to 20° C. The reaction mass was filtered and the residue was leached with toluene and aqueous ammonia once again. The toluene layers were combined and the aqueous layer was separated. The toluene layer was washed repeatedly with aqueous ammonia and then with demineralized water. The toluene layer was concentrated to obtain crude citalopram base. Crude citalopram base (50 g) was dissolved in toluene (75 ml) and n-hexane (225 ml) was added dropwise. The resinous mass was separated and filtered through a bed of Hyflo®. The Hyflo® bed was washed with n-hexane (50 ml). The filtrates were combined and concentrated under vacuum to give citalopram base in molten form (21 g). 20 g of citalopram base so obtained was dissolved in toluene (100 ml), activated carbon (1 g) and silica (1 g) were added and the mixture stirred for 30 minutes. The bed was washed with toluene (20 ml). To the combined toluene extracts (120 ml); toluene (80 ml) and water (100 ml) were added. The pH of the aqueous layer was adjusted to 2.0±0.2 with aqueous hydrobromic acid. The aqueous layer was extracted twice with toluene (200 ml) and separated (after each extraction, the pH was checked and readjusted to 2.0±0.2). The pH of the aqueous layer was readjusted to 3.0±0.2 using 10% aqueous sodium hydroxide, extracted twice with toluene (200 ml) and separated (after each extraction, the pH was checked and readjusted to, 3.0±0.2). The pH of the aqueous layer was adjusted to 4.0±0.2 using 10% aqueous sodium hydroxide and extracted twice with toluene (200 ml) and separated (after each extraction, the pH was checked and readjusted to 4.0±0.2). Subsequently, the pH of the aqueous layer was adjusted to 5.0 and then to 6.0±0.2 with 10% aqueous sodium hydroxide, extracted twice with toluene (100 ml) and separated (after each extraction, the pH was checked and readjusted to 5.0 and 6.0±0.2 each time). The pH of the aqueous layer was adjusted to 11.5±0.2 with 10% aqueous sodium hydroxide and extracted with toluene (3×75 ml). The toluene layers were combined and washed three times with dimineralized water (5 ml). The toluene layer was concentrated to give citalopram base as a molten or oily mass. In another flask, a solution of oxalic acid in ethyl acetate was prepared by heating to a temperature of 65 to 70° C. The solution was cooled to 55 to 60° C. and added to the base in ethyl acetate at a temperature of about 50 to 55° C. The resultant solution was stirred at 65° C. for about 30 minutes, before being cooled slowly to 0 to 5° C. and filtered. The oxalate salt was washed with chilled ethyl acetate and n-hexane and dried. The dried oxalate salt so obtained was dissolved in water. The salt was converted to the free base using 5% aqueous sodium hydroxide and extracted in toluene. The aqueous layer was repeatedly extracted with toluene. The combined toluene layers were washed with aqueous dilute hydrobromic acid, then with dimineralized water and the toluene was distilled off under vacuum. Any traces of toluene were removed, isopropyl alcohol was added and the resultant solution was treated with activated carbon at 40 to 45° C. The solution was then filtered and aqueous hydrobromic acid was added at 30 to 35° C. to obtain a pH of 5.4 to 5.5. The resultant solution was cooled to 0 to 5° C., filtered and dried to give pure citalopram hydrobromide.

Yield and Purity

The yield of 1-(4'-fluorophenyl)-1-3-dimethylaminopropyl)-5-phthalane-carbonitrile purified by process I was 70 g. Citalopram hydrobromide thus purified meets the required degree of purity for pharmaceutical applications.

Citalopram hydrobromide so obtained can be further purified by crystallization from water, the recrystallized product melting at 182–185° C. Thus, the product obtained by crystallization from isopropyl alcohol was dissolved in the required quantity of water and allowed to crystallize, filtered and dried. If required, activated carbon may be used to improve the colour of this product during crystallization. The dried recrystallization citialopram hydrobromide may be milled using conventional procedures to give a crystalline powder suitable for formulation. Typically, 90% of the particles obtained after milling have a particle size of less than about 150 $\mu$m, 50% having a particle size of less than about 50 $\mu$m.

What is claimed is:

1. A process for preparation of 1-(4'-flurophenyl)-1-(3-dimethylaminopropyl)-5-phthalanecarbonitrile of the formula (I), or a pharmaceutically acceptable salt thereof,

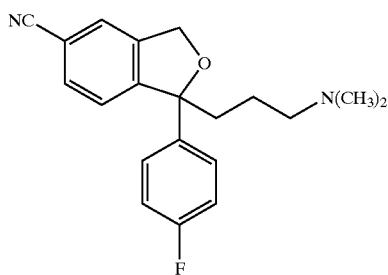

(I)

which comprises the step of preparing 2-hydroxymethyl-4-halo-4'-fluorobenzophenone of the formula (IV)

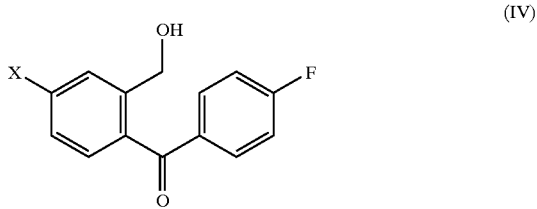

(IV)

by reacting a magnesium halide with a 5-halophthalide of the formula (II)

(II)

wherein X represents halogen, to form a 5-halophthalide/magnesium halide adduct, and reacting the adduct so obtained with a Grignard reagent of the formula (III)

(III)

wherein Y represents halogen to form the 2-hydroxymethyl-4-halo-4'-fluorobenzophenone of the formula (IV) and the reacting the 2-hydroxymethyl-4-halo-4'-fluorobenzophenone of the formula (IV) with a Grignard reagent of the formula (V)

(CH$_3$)$_2$N—(CH$_2$)$_3$—MgZ  (V)

to form a 1-(4-halo-2-hydroxymethylphenyl)-1-(4'fluorophenyl)-1-(3-dimethyl-aminopropyl)methanol of the formula (VI)

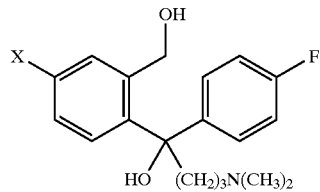

(VI)

and subjecting it to dehydration to form a 1-(4'-fluorophenyl)-1-(3-dimethylaminopropyl)-5-halophthalane of the formula (VIII)

(VIII)

and then reacting the formula (VIII) compound with a cyanating agent to form 1-(4'-fluorophenyl)-1-(3-dimethylaminopropyl)-5-phthalanecarbonitrile of the formula (I).

2. A process as claimed in claim 1, wherein the crude 1-(4'-fluorophenyl)-1-(3dimethylaminopropyl)-5-phthalanecarbonitrile of formula (I) is converted into an acid addition salt thereof by reacting it with an acid to form the acid addition salt and then extracting the acid addition salt into an aqueous phase of a bi-phasic solvent system.

3. A process as claimed in claim 2, wherein the 1-(4'-fluorophenyl)-1-(3-dimethylaminopropyl)-5-phthalanecarbonitrile of formula (I) is converted into its hydrobromide, acetate or oxalate salt by reacting the formula (I) compound with hydrobromic acid, ethyl acetate or oxalic acid, respectively.

4. A process as claimed in claim 2, wherein the acid addition salt is purified by recrystallization from a solvent, wherein the solvent is water, by dissolving the acid addition salt in water and allowing it to crystallize, and then subjecting it to filtering and drying.

* * * * *